(12) United States Patent
Neuberger

(10) Patent No.: US 8,721,631 B2
(45) Date of Patent: May 13, 2014

(54) TWISTER FIBER OPTIC SYSTEMS AND THEIR USE IN MEDICAL APPLICATIONS

(75) Inventor: Wolfgang Neuberger, Dubai (AE)

(73) Assignee: Biolite Pharma Marketing Ltd, F.T. Labuon (MY)

( * ) Notice: Subject to any disclaimer, the term of this patent is extended or adjusted under 35 U.S.C. 154(b) by 585 days.

(21) Appl. No.: 12/714,155

(22) Filed: Feb. 26, 2010

(65) Prior Publication Data
US 2011/0160713 A1 Jun. 30, 2011

Related U.S. Application Data

(60) Provisional application No. 61/245,484, filed on Sep. 24, 2009, provisional application No. 61/293,464, filed on Jan. 8, 2010.

(51) Int. Cl.
*A61B 18/16* (2006.01)
(52) U.S. Cl.
USPC .................... 606/15; 606/14; 606/13
(58) Field of Classification Search
USPC .................... 606/15, 14, 13
See application file for complete search history.

(56) References Cited

U.S. PATENT DOCUMENTS

| 5,416,878 | A  | * | 5/1995  | Bruce .......................... 600/108 |
| 5,553,177 | A  | * | 9/1996  | Hering et al. .................. 385/31 |
| 2005/0131399 | A1 | * | 6/2005 | Loeb et al. ..................... 606/15 |
| 2006/0285798 | A1 | * | 12/2006 | Brekke et al. .................. 385/47 |
| 2007/0167937 | A1 | * | 7/2007 | Brown ........................... 606/15 |

* cited by examiner

*Primary Examiner* — Kinam Park
(74) *Attorney, Agent, or Firm* — B J Associates; Bolesh J. Skutnik

(57) ABSTRACT

An improved device and method for safe, accurate and efficient surgical procedures are disclosed. The disclosed device is an optical fiber set with an asymmetric distal end configuration, comprising a bent tip fiber with a fused sleeve as an integral part of it, placed at the fiber's distal (output) end and with a rotatable connector at the proximal (input) side. Fiber tip and tissue-contacting surface located at the distal end of the tip may be constructed with different shape configurations, such as convex tip to improve focusing characteristics, concave tip to achieve diverging irradiation or an expanded beam tip to achieve an effect similar to that obtained by electrosurgical tools. A grip guarantees and enhances the ability to twist and rotate it easily. In another preferred embodiment, twisting maneuvers are enhanced through a special configuration. Both special features (bent tip and rotatable connector), allow for improved and enhanced treatment of diverse pathologies, making possible to efficiently and easily reach and treat specific tissues. Optical fiber's steerability, twistability and rotation lead to a more precise and improved effect on tissues.

26 Claims, 14 Drawing Sheets

US 8,721,631 B2

TWISTER FIBER OPTIC SYSTEMS AND THEIR USE IN MEDICAL APPLICATIONS

DOMESTIC PRIORITY UNDER 35 USC 119(E)

This application claims the benefit and priority of U.S. Provisional Application Ser. No. 61/245,484 filed Sep. 24, 2009, and U.S. Provisional Application Ser. No. 61/293,464 filed Jan. 8, 2010, each entitled "Twister Fiber Optic Systems and their Use in Medical applications" by Wolfgang Neuberger, which are incorporated by reference herein.

BACKGROUND OF THE INVENTION

1. Field of the Invention

The present invention relates to laser systems for medical treatments and in particular, for laser surgical procedures. More particularly, it relates to optical fiber systems and methods used for the treatment of various surgical procedures, including benign prostatic hyperplasia.

2. Information Disclosure Statement

Many important medical conditions suffered by many patients require treatments which consist in removing abnormal soft tissue from the body. Undesired tissue may include tumors and atheromatous plaques, excess fat in aesthetic treatments, or portions of prostate tissue. In urology, for example prostate disorders such as cancer or benign enlarged prostate (BPH) require this tissue to be partially or totally removed.

Tissue removal can be performed by means of different methods. Independently of the method used, the main objective of this kind of treatment is the removal of the whole undesired tissue while preventing from damage of surrounding tissue. In recent years, laser energy has been used in order to accomplish this aim.

Based on laser energy applied on tissue, numerous approaches have been proposed. Laser techniques are usually preferred due to its special capacity of delivering high amounts of power on reduced areas, thus improving treatment precision and accuracy and diminishing undesired effects on surrounding tissue.

Prostate cancer affects over 232,000 men in the US every year. It is a malignant tumor growth that consists of cells from the prostate gland. The tumor usually grows slowly and remains confined to the gland for many years. During this time, the tumor produces little or no symptoms or outward signs (abnormalities on physical examination). As the cancer advances, however, it can spread beyond the prostate into the surrounding tissues. The cancer can also metastasize throughout other areas of the body, such as the bones, lungs, and liver. When detected before metastasis, laser surgery employing side-firing fibers is currently a preferred treatment among surgeons and patients. It causes little blood loss and allows for a shorter recovery time.

Benign prostatic hyperplasia (BPH) or "enlarged prostate" refers to the noncancerous (benign) growth of the prostate gland. While BPH is the most common prostate problem in men over 50 years of age, benign growth of the prostate begins with microscopic nodules around 25 years of age but rarely produces symptoms before a man reaches 40. It is estimated that 6.3 million men in the United States have BPH and the disease is responsible for 6.4 million doctor visits and more than 400,000 hospitalizations per year.

The exact cause of BPH is unknown but it is generally thought to involve hormonal changes associated with the aging process. Testosterone likely has a role in BPH as it is continually produced throughout a man's lifetime and is a precursor to dihydrotestosterone (DHT) which induces rapid growth of the prostate gland during puberty and early adulthood. When fully developed, the prostate gland is approximately the size of a walnut and remains at this size until a man reaches his mid-forties. At this point the prostate begins a second period of growth which for many men often leads to BPH later in life.

In contrast to the overall enlargement of the gland during early adulthood, benign prostate growth occurs only in the central area of the gland called the transition zone, which wraps around the urethra. As this area of the prostate grows, the gland presses against the urethra, leading to difficult or painful urination. Eventually, the bladder itself weakens and loses the ability to empty by itself.

Obstructive symptoms of BPH such as intermittent flow or hesitancy before urinating can severely reduce the volume of urine being eliminated from the body. If left untreated, acute urine retention can lead to other serious complications such as bladder stones, urinary tract infections, incontinence, and, in rare cases, bladder and kidney damage. These complications are more prevalent in older men who are also taking anti-arrhythmic drugs or anti-hypertensive (non-diuretic) medications. In addition to the physical problems associated with BPH, many men also experience anxiety and a reduced quality of life.

Mild symptoms of BPH are most often treated with medication such as alpha-blockers and anti-androgens. Men suffering with moderate to severe BPH symptoms typically must undergo surgery. There are a number of different laser techniques in which light is used to eliminate excess prostate tissue either by ablation (vaporization), thermal coagulation or a combination of these mechanisms. The observed clinical effects are due to the absorption of light (by the target tissue itself and/or surrounding fluids) and subsequent heat transfer, the extent of which largely depends on the power and wavelength of the laser beam.

Many types of laser surgeries are able to provide a near-immediate improvement in the urinary stream. Laser surgery for BPH can have other potential advantages such as reduced blood loss as well as shorter treatment times, faster patient recovery, and a lower risk of post-treatment incontinence, depending on the wavelength and technique used. However, many patients still require catheterization for 1-2 weeks post-treatment after undergoing some forms of laser surgery.

An important factor determining the success of laser surgery in urology is the accuracy with which the surgeon is able to eliminate undesired prostate tissue to achieve adequate tissue ablation without damaging surrounding healthy tissue. Accuracy is defined not only in mechanical terms but also in confinement of the treatment beam, whether or not significant decanting of the tissue occurs before ablation, and other concerns. To achieve some success, inventors have worked over the years on developing optical fiber configurations that can improve efficiency, accuracy and thus safety of the procedure. Fibers must also be able to withstand the high laser energy emitted by new laser source technologies. In BPH treatment, laser beams oriented at a certain angle with respect to the main fiber axis are preferred, for more effective tissue ablation. U.S. Pat. No. 5,292,320 by Brown et al. discloses a side firing output end having multiple side fire surfaces within the fiber core. The fiber core has a plurality of grooves as well as a slanted end surface for reflecting laser energy in a lateral manner. This approach helped efficiency but was a complex structure to make, and if care was not exercised working tip could be fragile. Furthermore since the core is glued into the end cap, under high power laser operations, for example, 50 W or greater, this output end often fails.

U.S. Pat. No. 5,509,917 by Cecchetti et al. disclose a lateral beaming laser tip having a transparent quartz cap about the output end of the optical fiber therein. The cap is shown having various focusing means for the laser radiation reflected off of the slanted end surface of the optical core. This laser tip is generally complex to manufacture and connection to the underlying fiber also can be variable and difficult to repeatedly produce.

In U.S. Pat. No. 5,366,456, Rink et al. depict a laser cutting scalpel wherein the transmitted radiation is delivered at an angle to the incident radiation source and tool. The device has a firing tip which has an insert with a highly polished minor surface lying at a specific angle with respect to central longitudinal axis of the optical fiber. Thus, impinging laser radiation is reflected to the side and delivered at approximately a right angle to the fiber. The firing tip can be mounted on the tip of a cannula, the entire apparatus being rotatable about the central axis of the fiber. Brekke et al. in U.S. Patent Publication 2006/0285798 claim a bent side-firing laser for redirecting light laterally relative to an axis of the apparatus. Various aspects of the construction and use of the fiber are complex and potentially difficult to reproduce uniformly from case to case. In U.S. Pat. No. 5,428,699, Pon discloses an optical fiber for laterally directing a laser beam similar to Brown and Cecchetti where thick claddings are used to decrease scattered electromagnetic radiation from the internal reflecting structure and thereby improving the efficiency of the laterally directing probe. All three previously mentioned patents claim that radiation beam is emitted laterally with respect to probe's main axis, in a non-contact mode. They improve some features over the prior art, though many of the shortfalls of laterally firing systems remain, including how to maintain uniform non-contact and keep from 'fouling' of the active emitting surface.

U.S. Pat. No. 5,553,177 by Herring et al. depicts a light-guiding device that consists of a section of a lightguiding material which has been bent at an angle of about 90 degrees relative to the axis of light transmission with a small bend radius. The output is radiated asymmetrically from the fiber axis. The bent section is treated to obtain a homogenous refractive index in the lightguide's core. Problems here are difficult to form small sharp angle, often a fragile structure, especially, in smaller dimensioned fibers. In U.S. Pat. No. 5,416,878, Bruce depicts a side firing laser fiber in which the output end terminates in a flat face having an accurate edge around its circumference. It has a bend close to the emitting face of the fiber which results in a laser beam directed at a certain angle from the longitudinal axis of the main body of the optical fiber. Here, the difficulty of rotational movements by the surgeon represents a main drawback. Also while some improvements in forming shallower bend, the tip is still somewhat subject to accidental breakage. Another disadvantage, is that both inventions present a flat surface end, limiting light focusing characteristics of fiber, which becomes important, for example, if steam bubbles appear in front of fiber, a common situation at high powers. Furthermore, flat surface may damage or perforate non target tissue as well.

U.S. Pat. No. 6,699,239 by Stiller et al. discloses a laser instrument for vaporization of biological tissue and stabilization of the application cap during tissue removal. The laser instrument includes an optical waveguide with a light guide portion that emits light and an application cap coupled to the optical waveguide that transmits light. The laser instrument can be inserted into an endoscope and extended or retracted to position the application cap for vaporization and removal of biological tissue. This invention presents some characteristics which represent important drawbacks. For instance, fiber tip is fused with receiving sleeve, but optical waveguide is joined mechanically to the application guide by means of bonding between the sheathing and the receiving sleeve. This renders device potentially vulnerable to deterioration when high temperatures are present, and if high energy is applied, end cap may become detached while inside body, representing a hazard for the patient and a complication for the surgeon. Furthermore, end cap is composed of two parts, mainly a fiber positioned within a curved glass end. Therefore, in a liquid medium such as inside the urethra, laser radiation is transmitted through the material of end cap, that is, from the outer area of the curved part of the probe and emerging from multiple sites. This may represent a difficulty for the surgeon as it is difficult to point radiation in a precise direction so healthy tissue will also be damaged. This fact also renders a reduction in power density. Finally, due to optical coupling between fiber and cap, light losses and reflection could diminish efficiency of treatment.

As can be seen from previously mentioned patents, prior inventions present several drawbacks, such as those related to difficulty of maneuvering, focusing possibilities and energy limitations. Prior art is also limited in that treatment is not always as effective as desired as they are time consuming. As newer technologies arise, physicians strive for achieving shorter procedure times to satisfy their patients, and at the same time to be able to treat more patients daily.

There is thus a need for a laser treatment system that improves on the state of the art, providing a better, more robust, fiber tool to enhance speed of removal, ease of handling/working, while maintaining the benefits of laser cutting. The present invention addresses these needs.

OBJECTIVES AND BRIEF SUMMARY OF THE INVENTION

It is an objective of the present invention to provide a device and method for improved surgical procedures, such as urological treatments, and tissue ablation.

It is also an objective of the present invention to provide a device and method for faster, more precise, safer and more reliable treatment to achieve effective laser radiation while preserving surrounding tissue.

It is another objective of the present invention to provide a device and method for improved laser surgical procedures, enhanced by fiber steerability, free rotation and special asymmetric distal end configurations.

It is yet another objective of the present invention to more easily treat benign prostatic hyperplasia by means of high power vaporization of prostatic tissue as well as lobe excavation.

It is yet another objective of the present invention to provide a surgical device and method for the removal of tumorous or hyperplasic tissue or other unwanted tissue in the body in an improved, efficient manner.

Briefly stated, an improved device and method for safe, accurate and efficient surgical procedures are disclosed. The disclosed device is an optical fiber set with an asymmetric distal end configuration, comprising a bent tip fiber with a fused sleeve as an integral part of it placed at the fiber's distal (output) end and with a rotatable connector at the proximal (input) side. Fiber tip and tissue-contacting surface located at the distal end of the tip may be constructed with different shape configurations, such as convex tip to improve focusing characteristics, concave tip to achieve diverging irradiation or an expanded beam tip to achieve an effect similar to that obtained by electrosurgical tools. A grip guarantees and enhances the ability to twist and rotate it easily. In another preferred embodiment, twisting maneuvers are enhanced through a special configuration. Both special features (bent tip and rotatable connector), allow for improved and enhanced treatment of diverse pathologies, making possible to efficiently and easily reach and treat specific tissues. Optical fiber's steerability, twistability and rotation lead to a more precise and improved effect on tissues. Due to this, easier, faster and more precise and efficient treatments can be performed by its means. For instance, it may be inserted into a cystoscope to perform high power ablation of prostatic tissue for BPH treatments, or steered into one of the prostatic lobes, which can be excavated from the inside in order to relieve pressure on the urethra while maintaining the urethra's integrity. Other uses might be the removal of tumorous, hyperplasic or other unwanted tissue in the body. Optical fiber set disclosed can be used with laser sources of various wavelengths, including dual laser sources, but also higher power LED devices or very bright light sources can be used to generate the radiation to be transmitted as well. Due to this novel design, described fiber is easy to put in place, also easy to maintain in contact with tissue and highly durable. The feel to the doctor is greatly improved too. This results in more effective power transfer into tissue and therefore procedures are more reliable and procedure times are cut by up to 30%.

The above and other objects, features and advantages of the present invention will become apparent from the following description read in conjunction with the accompanying drawings.

DETAILED DESCRIPTION OF PREFERRED EMBODIMENTS

Figure 1A:
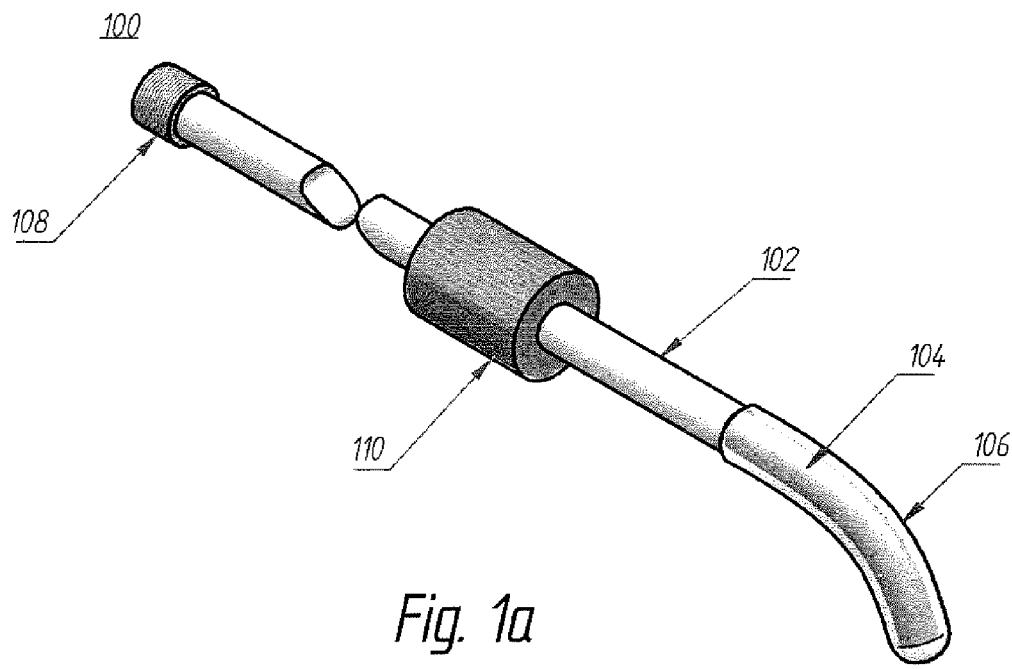
FIGS. 1a and 1b depict a preferred embodiment of present invention in which optical fiber set comprises a bent tip, a fused cap, a rotatable connector and a grip.

According to prior art, medical laser fibers are generally configured externally concentric to the fiber main axis, for instance, bare fibers, ball tipped fibers, conical fibers or side-emitting fibers.

When used for surgical procedures, these fibers have evident shortcomings. Fiber maneuverability can be inappropriate, leading to a poor outcome and diminished efficiency. Furthermore, when these kinds of fibers come inadvertently into contact with the tissue during non-contact procedures, burnt fibers and breakage may occur, as well as unwanted damage to tissue. In addition, prior art's optical fibers lack simple, effective and precise steerability and rotation features, which can make it difficult for the practitioner to maneuver with confidence, and thus represent a drawback when treating many pathologies like benign prostatic hyperplasia (BPH). Due to this, tissue excavation and steering can be difficult, and slow leading to longer more stressful procedures and generally slower recovery for patients.

The present invention discloses an improved device and method for safe and efficient surgical light procedures. The device disclosed in the present invention is an optical fiber set with an off-axis configuration, consisting of a bent tip fiber with a fused sleeve as an integral part of it, placed at its distal (output) end and with a rotatable connector at the proximal (input) side. Fiber shape may be described as an axially-extending portion defining an elongated axis, an axially-extending tip portion located at the distal end of the fiber and oriented at an obtuse angle relative to elongated axis, and a tissue-contacting surface located at the distal end of the tip portion. A grip guarantees and enhances the ability to twist and rotate it easily.

Numerous advantages arise when performing surgical procedures with the disclosed invention. First, the procedure is rendered faster and more efficient. Since the fiber can be kept in contact with the tissue, energy loss due to fiber degradation is practically zero. Also stray light from the fiber tip, is substantially non-existent as the light exits from only the fiber tip. In turn, fiber durability is considerably longer because of the structure, overcoming early failure issues with prior art fibers. Finally, at preferred wavelengths, bleeding is not observed during the procedure, resulting in an excellent field of view and visibility of the treated area and fiber tip.

The device disclosed in the present invention, can be inserted, for instance, into a cystoscope to perform high power ablation of prostatic tissue for BPH treatments. Furthermore, it can be steered into one of the prostatic lobes, to excavate tissue from the inside in order to immediately relieve pressure on the urethra while maintaining the urethra's integrity as much as possible. In addition, several other benefits are obtained. For instance, with its familiar feel the surgeon can more easily handle the fiber tip in the apex and critical areas, like sphincter and verumontanum. Procedure can be easily and effectively carried out with commercially available cystoscopes.

Other uses might be the removal of tumorous, hyperplasic, or other unwanted tissue in other areas within the body.

Figure 1B:
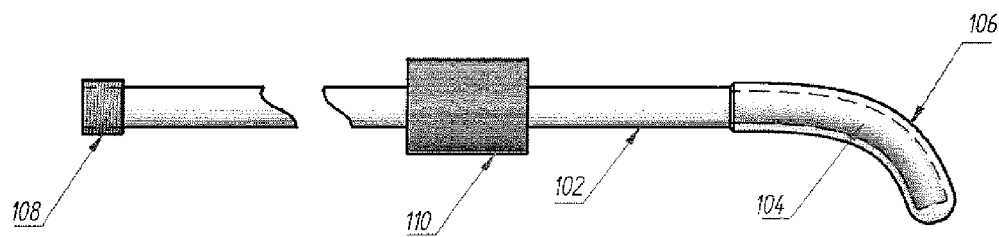

FIGS. 1a and 1b schematically depict a preferred embodiment in which twister optical fiber set 100 comprises an optical fiber, composed by jacketed fiber 102 and clad/core 104, fused sleeve/cap 106, rotatable connector 108 and grip 110. Optical fiber's distal end is composed of bent-tip fiber clad/core 104 and fused sleeve 106, designed as an integral part of it. Sleeve extends annularly about the tip portion. Axially-extending clad/core 104 defines the emitting face, and the emitting face of the clad/core and distal portion of the sleeve 106 define the tissue-contacting surface. Fused sleeve 106 would typically be about 15 cm long. The clad/core fiber 104 could be a range of dimensions from about 50/10 μm to about 1800/1700 μm for the clad and core diameters respectively. Fused sleeve 106 is quartz and acts as reinforcement, allowing fiber to withstand high energies and handling common for most electrosurgical tools. Rotatable connector 108 is placed at the proximal (input) end of optical fiber set 100, permitting the free rotation and twistability of optical fiber. Grip 110 guarantees and enhances the ability to twist and rotate it easily. This allows the surgeon to make smoother, more precise movements in circular fashion. Grip can be positioned in different places along optical fiber and designed with different shapes, according to the treatment requirements and physician preferences. Both special features (bent tip and rotatable connector), allow for improved and enhanced treatment of diverse pathologies, making it possible to efficiently and easily reach and treat specific tissues internally.

Figure 1C:
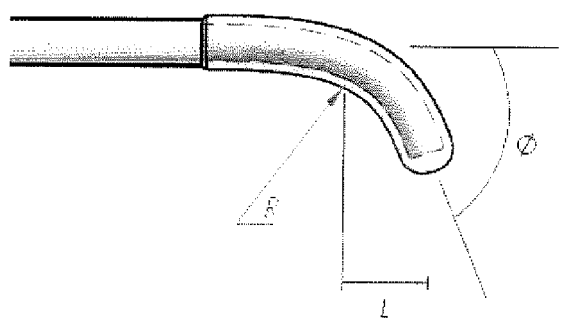
FIG. 1c schematizes a preferred embodiment of present invention showing the optical fiber tip and its angle notation.

FIG. 1c schematizes a preferred embodiment of the present invention showing the optical fiber tip and its angle rotation. Axially-extending tip portion defines an axial length, L, within the range of about 2 mm to about 5 mm. It is important to note that different combinations of radius and angles can be used to develop this fiber. The exact values of radius and angles will be chosen according to the treatment to be performed, considering accessibility, tissue characteristics, scope size, etc. In a preferred embodiment, axially-extending tip portion located at the distal end of the fiber is oriented at an angle, φ, of about 20° to about 40° relative to elongated axis.

Figure 1D:
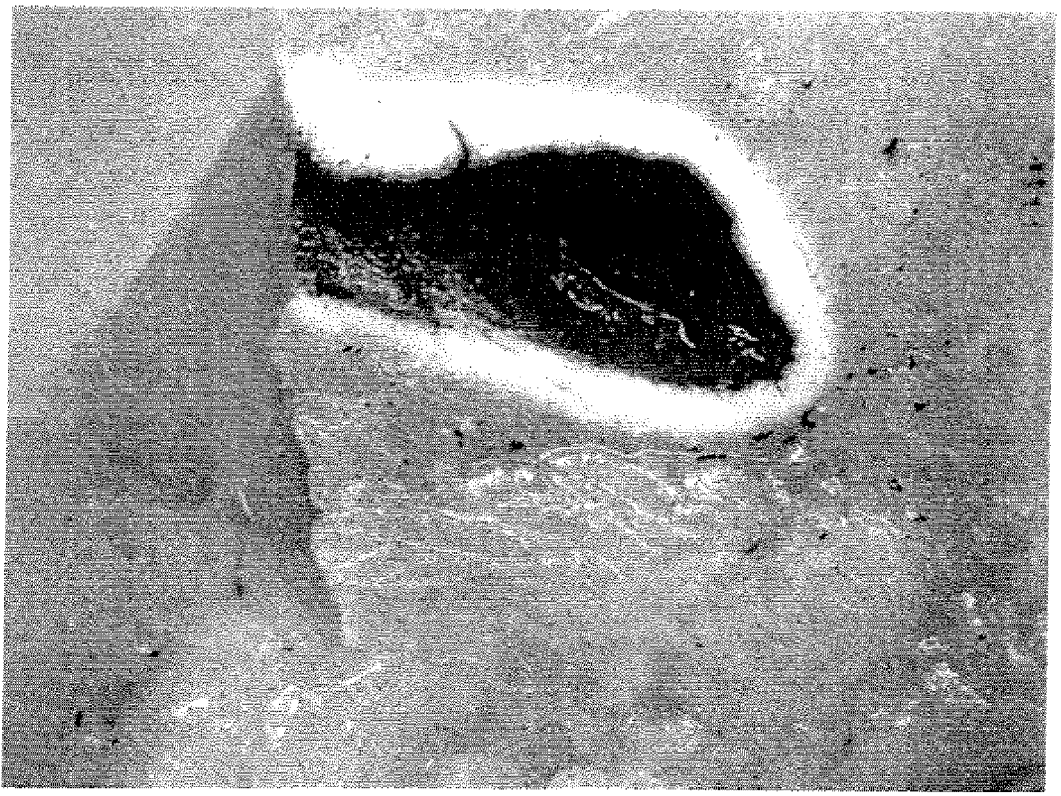
FIG. 1d depicts a picture of a tissue treated with the device disclosed in the present invention.

FIG. 1d depicts a picture of a tissue treated with the device disclosed in the present invention. It can be appreciated that optical fiber's enhanced steering, twisting and rotation capabilities help achieving an improved effect on tissues. Due to this, easier, faster and more precise and efficient treatments can be performed by means of the device and method disclosed in the present invention.

Figure 2A:
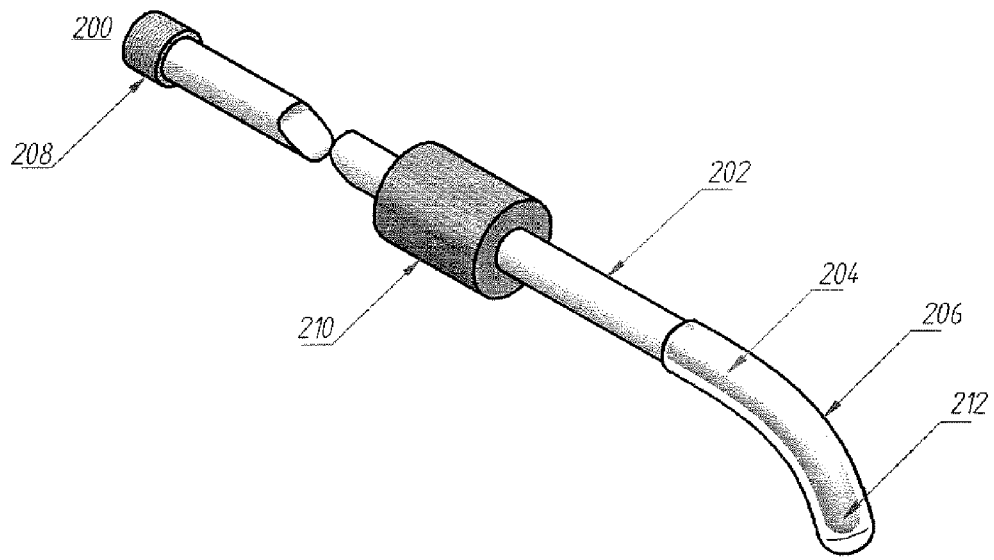
FIGS. 2a and 2b show a preferred embodiment of present invention in which optical fiber comprises a rounded concave tip.
Figure 2B:
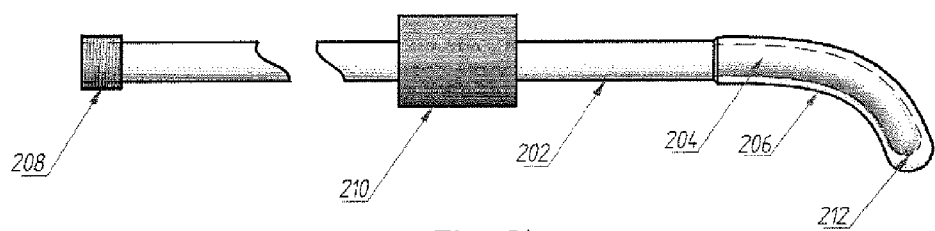
Figure 2C:
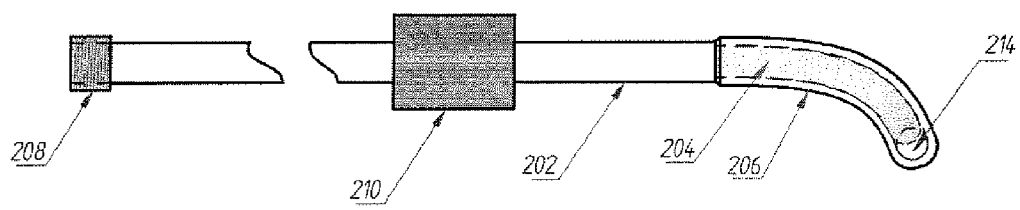
FIG. 2c schematizes a preferred embodiment of present invention in which optical fiber comprises rounded concave gap at its concave tip.
Figure 2D:
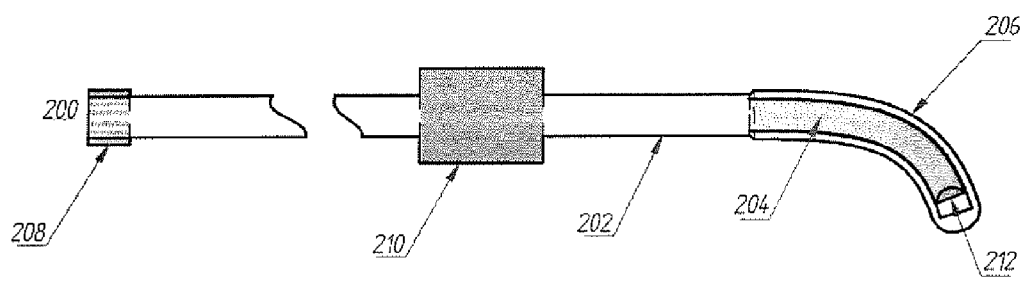
FIG. 2d shows a preferred embodiment of present invention in which optical fiber comprises a rounded convex tip.

FIGS. 2a, 2b, 2c and 2d show preferred embodiments of present invention in which, fiber tip is rounded in a lens-shaped output end so as to focus the transmitted radiation according to specific treatment effect. Twister optical fiber set 200 comprises an optical fiber, composed by clad 202 and core 204, fused cap 206, rotatable connector 208 and grip 210. Optical fiber's distal end is composed of bent-tip fiber 204 and fused sleeve 206, designed as an integral part of it. Emission tip 212 can be either convex as in FIGS. 2a and 2b when radiation is desired to converge. Emission tip 212 may have a concave gap 214 of a specific refraction index as shown in FIG. 2c, to alter focus characteristics and as a consequence, to achieve different radiation patterns. Alternatively, if radiation is desired to diverge to a determined focal point, FIG. 2d shows an embodiment in which emission tip 212 has a concave form to achieve this effect.

Figure 3A:
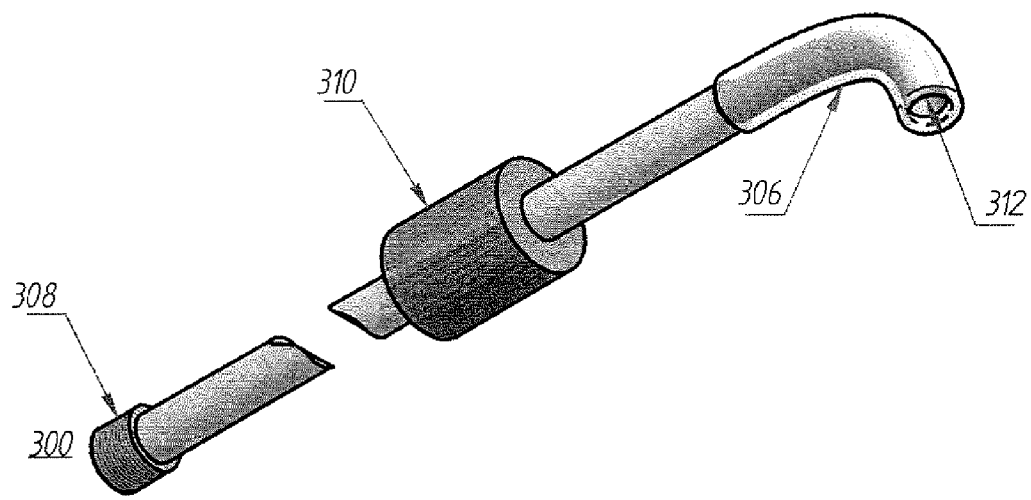
FIGS. 3a and 3b depict a preferred embodiment of present invention in which optical fiber comprises a covered tip.
Figure 3B:
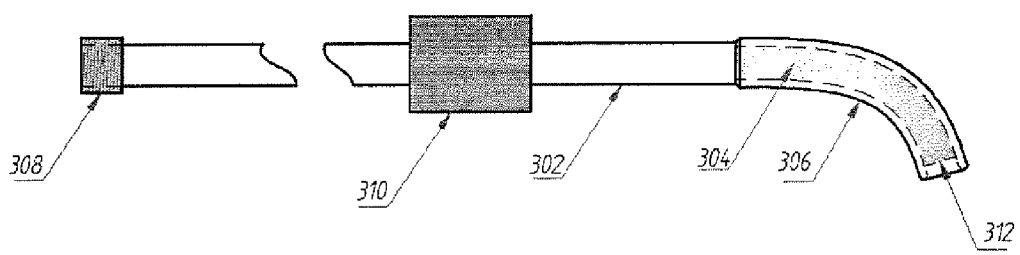

As shown in FIGS. 3a and 3b, in another embodiment, twister optical fiber set 300 includes covered reinforced emission tip. Optical fiber set 300 comprises an optical fiber 302 and clad/core 304, fused sleeve/cap 306, rotatable connector 308 and grip 310. Optical fiber's distal end is composed of bent-tip fiber 304 and fused sleeve 306, designed as an integral part of it. Fused sleeve/cap 306 would typically be about 15 mm long. From fused sleeve/cap 306 protrudes emission tip 312, thus protecting fiber from damage during treatment. When high laser power is emitted, vapor bubbles are usually formed. This special tip configuration keeps them in place, leading to shock wave formation and enhancing tissue removal. Furthermore, protruding fused rounded cap allows for an enhanced blunt tip configuration, preventing tissue from damage or scoring in forward movements, and also reducing chance of bleeding when power is off.

Figure 4:
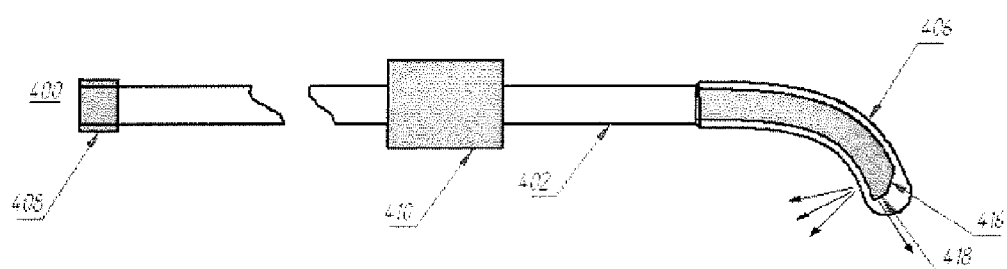
FIG. 4 shows a preferred embodiment of present invention in which optical fiber comprises an expanded beam tip.

In another preferred embodiment, the fiber end presents an expanded beam tip as shown in FIG. 4. This is achieved by designing fiber tip with slanted portion 416 and perpendicular portion 418. Optical properties of slanted portion 416 cause radiation to be emitted in a perpendicular axis and perpendicular portion 418 emits in a forward direction. As a consequence, laser radiation is emitted in a wider beam, mimicking effects of electrosurgical tools.

Figure 5A:
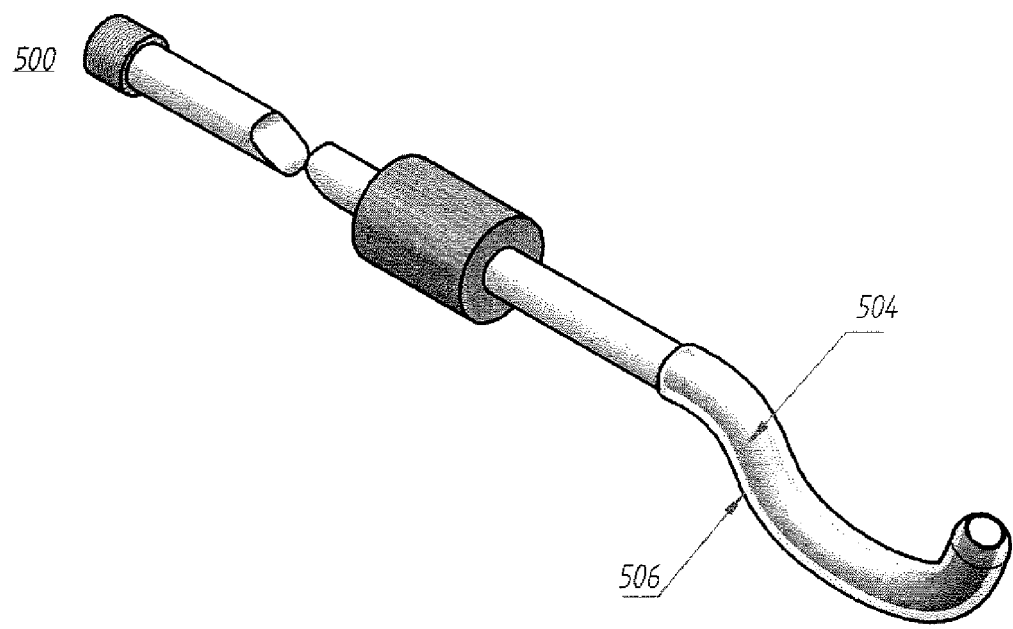
FIGS. 5a and 5b show a preferred embodiment of present invention in which optical fiber set design allows for improved twistability.
Figure 5B:
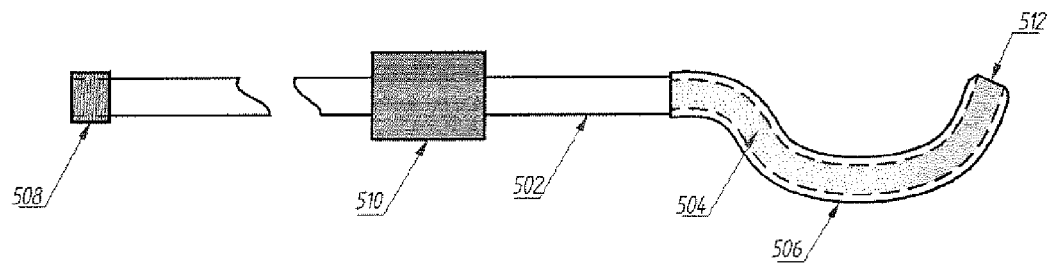

Sweeping method used by urologists can be improved by means of another embodiment in which fiber is shaped as in FIGS. 5a and 5b. Fused cap portion is curved such that fiber tip is on the same axis as fiber set. Thus, twisting capability is substantially improved as well as visibility down the scope. As in previous embodiments, tip can be designed to emit radiation at a number of angles with respect to main axis.

Figure 6A:
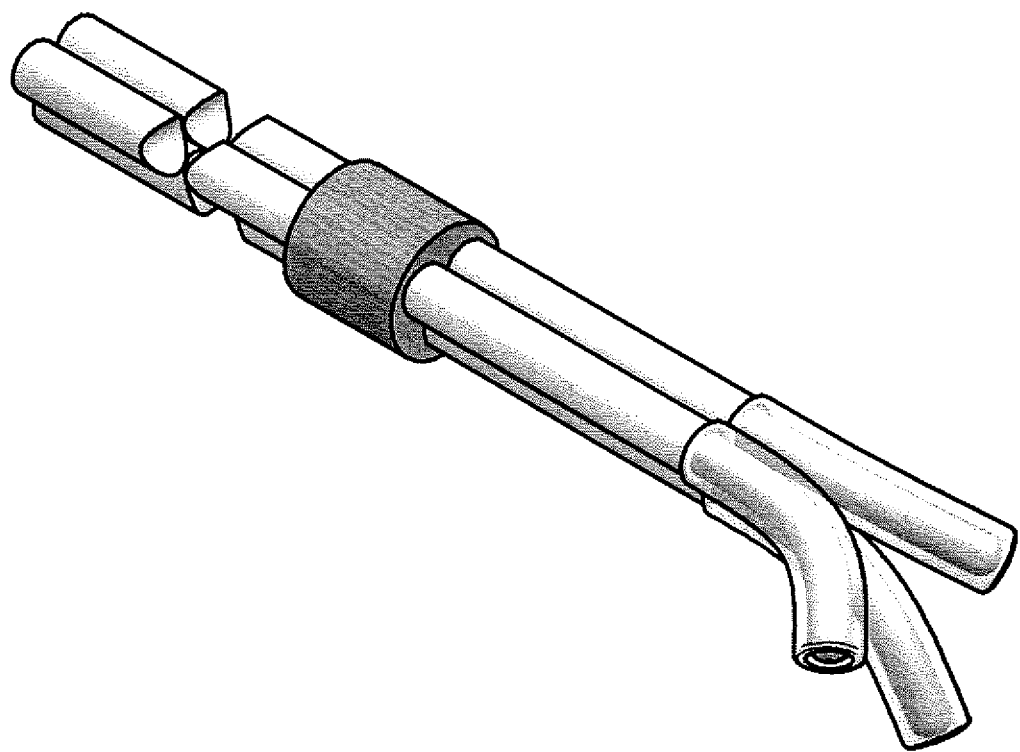
FIGS. 6a, 6b, 6c, 6d, and 6e depict a preferred embodiment of present invention combining 3 fibers into one bundle, which can be folded and unfolded.
Figure 6B:
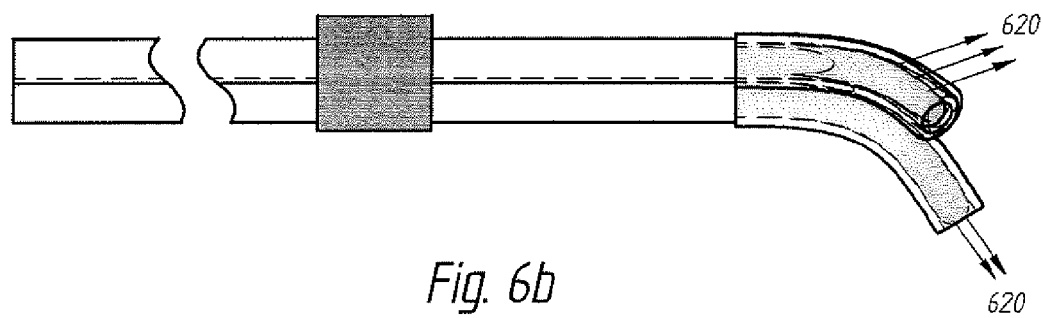
Figure 6C:
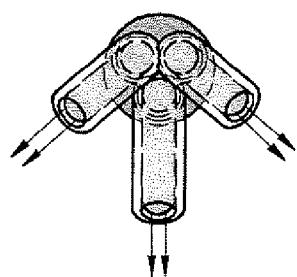
Figure 6D:
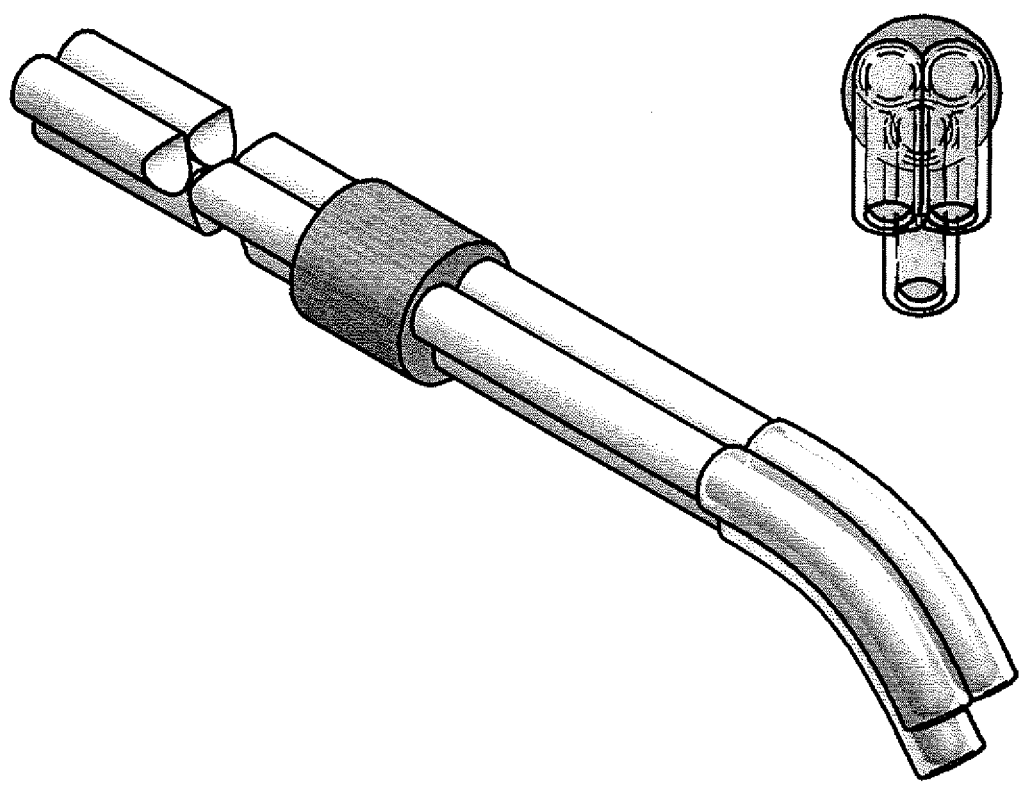
Figure 6E:
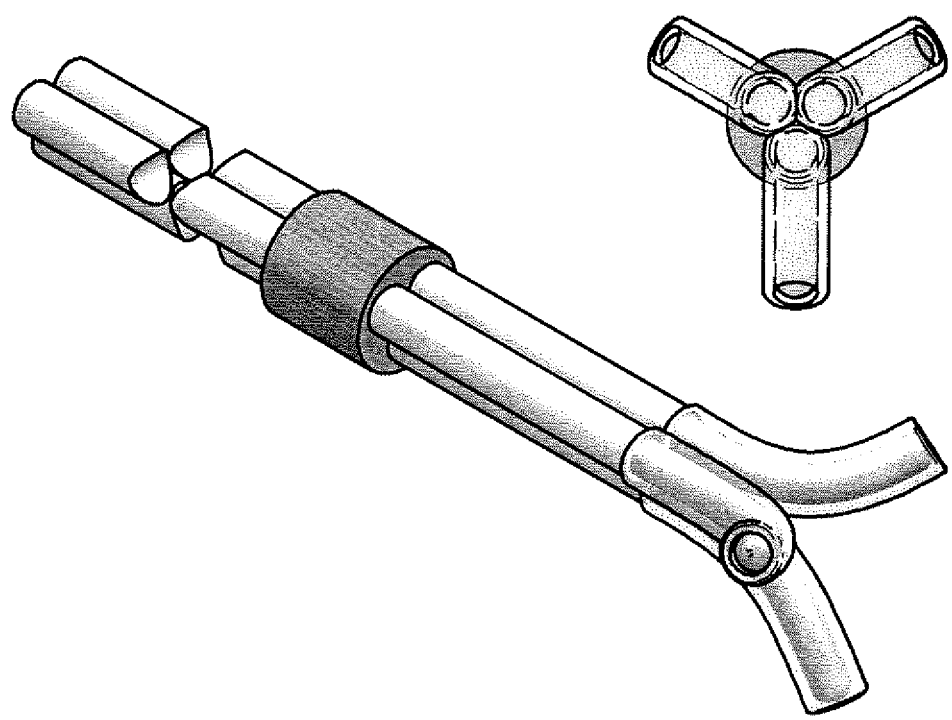

FIGS. 6a, 6b, 6c, 6d and 6e schematize another preferred embodiment of present invention. A variant of present invention is designed by combining three or more fibers in a close contact arrangement into one bundle as shown in FIG. 6a. FIGS. 6b and 6c depict laser radiation rays 620. As a consequence of this radiation pattern, it can be appreciated that with each forward lasing movement, carried out by physician, a large groove is produced, considerably decreasing procedure time and enhancing treatment efficiency. Additionally, twister fiber assembly has the capability of folding and unfolding, thus varying overall diameter. FIGS. 6a, 6b, and 6c show a partially unfolded bundle, whereas in FIGS. 6d and 6e fiber assembly is folded and completely unfolded, respectively. In shown embodiment, when bundle is totally unfolded, angle between fibers is about 120°, since it is comprised by three fibers. This feature helps the insertion into scopes or channels, such as a cystoscope normally used in urologic procedures. Furthermore, different unfolding properties could allow the modification of radiation patterns. For example, fiber assembly may unfold partially, totally or remain folded.

Figure 7A:
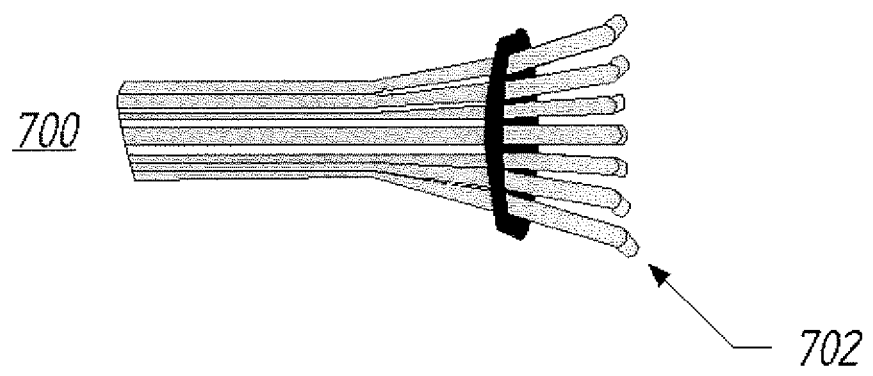
FIGS. 7a and 7b show a preferred embodiment of present invention with 7 fibers in a bundle configuration.
Figure 7B:
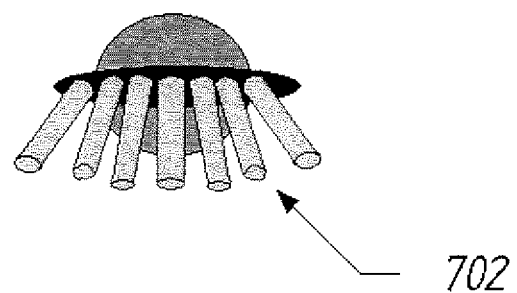

In another preferred embodiment, a number of fibers of small diameter can be bundled together in a close contact arrangement, each bent and reinforced, transporting a reduced amount of energy. This way, while they fit in a round configuration while in the scope, they splay out to cover a larger area in 'rake' fashion when deployed beyond scope end in operation. Also, since much smaller diameter fibers are used, laser radiation is distributed in a considerably smaller spot size. As a consequence, higher power density is achieved at fiber distal ends. As an example FIGS. 7a and 7b show a preferred embodiment of present invention in which 7 fibers 702 are arranged in a bundle 700, each having a core diameter ($D_1$) of 100 μm and used to transmit and irradiate at a power $P_1$ of 30 W. An important advantage can be appreciated when comparing power density $\delta_1$ at distal end of each fiber 702 in bundle 700 of this embodiment with power density $\delta_2$ at distal end of normally used 550 μm ($D_2$) fiber transmitting at a power $P_2$ of 180 W. Thus, $$\frac{\delta_1}{\delta_2} = \frac{\frac{P_1}{A_1}}{\frac{P_2}{A_2}} = \frac{P_1 D_2^2}{P_2 D_1^2} = \frac{30[W]550^2[\mu m]}{180[W]100^2[\mu m]} = 5.042$$

This result demonstrates that this embodiment offers over 5 times more power density, while using a 6 times lower laser power source (30 W vs. 180 W). As a consequence, treatment is rendered both more efficient and effective, using a simpler lower power laser device.

In another example, 7 fibers with a core diameter of 200 μm are arranged. In this example calculating as in previous example, yields 1.26 times higher power density. Once again, a higher power density is achieved with highly flexible fibers.

In yet another example with same fiber configuration, the same power density is obtained by using very low power source. For instance the same power density obtained with 180 W using 550 um core fibers can be achieved by applying just 6 W to the 100 um core fibers.

Output ends of fiber can be fused together or fused into a quartz glass device which would serve at the same time as a spacer. Connector ends can be arranged in a line configuration. With this special design, small diameter fibers can be bent forming a smaller radius, at much lower stress on the fiber surfaces. This results in easier insertion into smaller scopes, due to their flexibility as well as reduced mechanical stress. Furthermore, output beams can form a spread-out pattern, resulting in a broader ablation zone, therefore removing tissue more evenly and faster.

Radiation pattern formed by output beam will depend on bundle arrangement. Fiber tips can come out with all pointing in the same direction for a more concentrated and localized irradiation, splay out radially forming a conical beam or any combination of these according to desired effect.

Figure 8A:
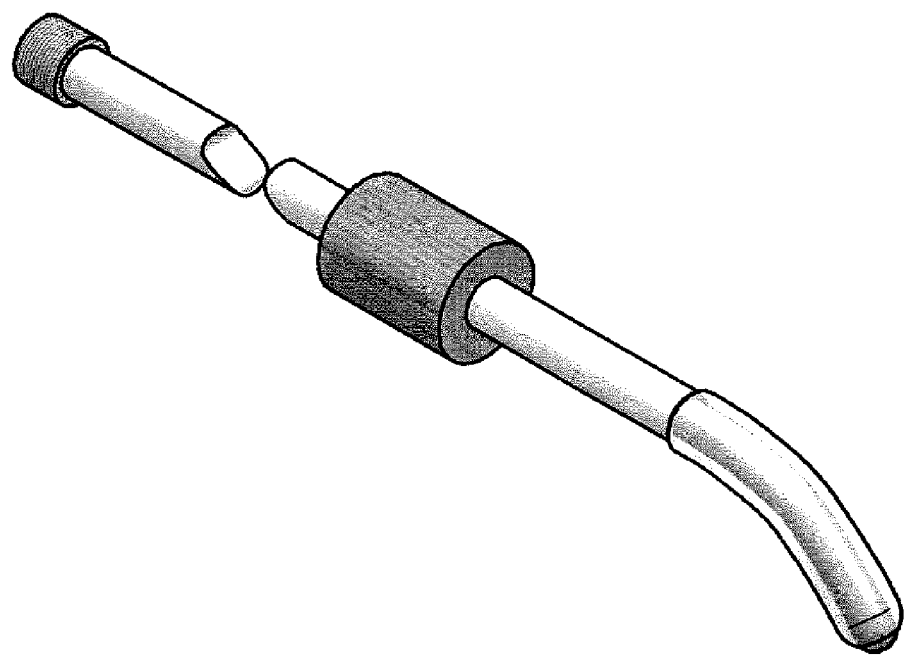
FIGS. 8a and 8b schematize another embodiment of present invention in which fiber is inclined relative to tissue surface.
Figure 8B:
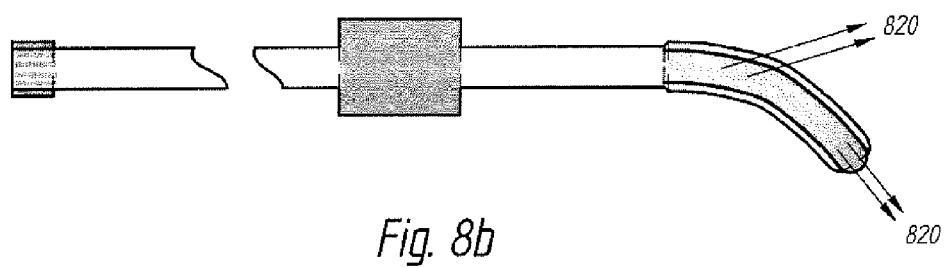

In another preferred embodiment fiber is designed for using it inclined relative to tissue surface, as shown in FIG. 8a. Radiation pattern 820, as schematized in FIG. 8b, causes a wider shallow groove on tissue. This is useful when thin superficial portions of tissue need to be removed without damaging underlying tissue.

Figure 9:
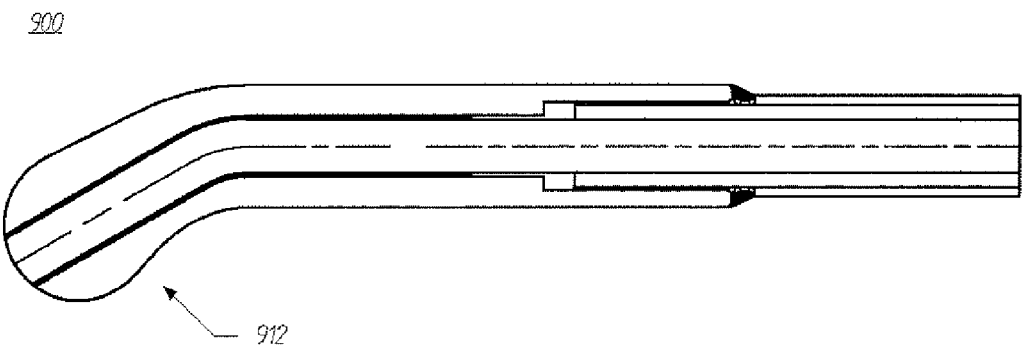
FIG. 9 depicts another embodiment of present invention with an enlarged area distal end.

In another preferred embodiment of present invention, as shown in FIG. 9, fiber 900 is slightly deformed at glass tip 912 such that at distal tip's output end, the core and fiber cross-section are expanded compared with these dimensions at fiber's proximal end resulting in an enlarged volume at the distal end of fiber 900. Tissue-contacting surface defines a thickness that is sufficient to allow it to wear during ablation of the tissue without preventing the passage of laser energy from the fiber therethrough and into the tissue. In a preferred embodiment, thickness is within the range of about 1 mm to about 4 mm. As emitting surface is now greater, this wear surface configuration results in lower power density of emitted radiation, which in turn, diminishes thermal loading significantly, thus improving mechanical, thermal and power stability. Furthermore, this special design increases fiber durability and lifetime.

Figure 10:
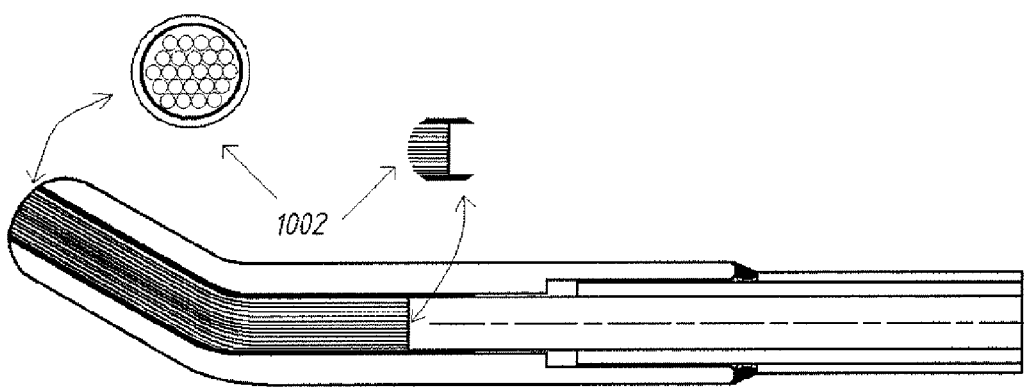
FIG. 10 depicts another preferred embodiment with many small collapsed fused fibers.

FIG. 10 depicts another preferred embodiment which consists of many small collapsed fused fibers 1002, enabling tighter bends and a minimum proportion of escaping beams. This can be achieved for example, with a 550, 715 or 900 μm end-capped with a specially fused and reinforced distal end where 30 to 40 very small diameter fibers, optimized for packing fraction, have been bent, fused and mated to the main fiber. This makes light transmission more efficient and therefore minimum energy levels need to be applied. In addition, this configuration broadens tissue contact, also making treatment more efficient. Greater efficiency in turn enhances precision and safety of the procedure as well as fiber durability. In another version of this embodiment, distal tip is allowed to be broadened in comparison with the main fiber's cross-section dimensions, thus creating a broader groove in the tissue.

Despite the fact that clad is shown in previous embodiment drawings ending at fused cap proximal end, it may be designed to reach fiber distal end.

In another embodiment of present invention, sweeping movement can be carried out by means of a motor. As a consequence, precise periodical sweeping movements can be achieved, thus diminishing physician stress considerably and enhancing patient safety. In addition, a motor within the grip, or otherwise placed along the proximal side of the fiber could provide vibration or a combination of different types of movements. Physician can choose the desired movement pattern according to the specific treatment, experience and personal preferences.

Twister optical fiber set disclosed can be used with laser sources of various wavelengths. In a preferred embodiment, wavelengths of 980 nm, 1470 nm, 1950 nm or combinations of these wavelengths in appropriate proportions can be used, with total combined power levels of 200 W or even more. For example, better and more efficient results have been obtained using a twister fiber set, having an off-axis distal end, with a 980 nm laser source in comparison to side fiber. In another example, use of a twister fiber set, as disclosed, with a laser source combining 1470 and 980 nm wavelengths results in a powerful, safe and easy BPH procedure. In both cases, due to improved efficiency, lower power levels were sufficient to obtain desired results, thus diminishing risk of damage to healthy tissue, and increasing fiber durability.

In other preferred embodiments, diode lasers, fiber lasers, and also higher power LED devices or very bright light sources can be used to generate the radiation to be transmitted as well.

In a preferred embodiment, twister optical fiber set might be inserted into a cystoscope to perform high power vaporization of prostatic tissue for BPH treatments. Furthermore, it may be steered into one of the lobes and said lobe tissue can be excavated from the inside to relieve pressure on the urethra while maintaining the urethra's integrity as much as possible intact.

In another preferred embodiment, optical fiber disclosed might be used to remove tumorous, hyperplasic, or other unwanted tissue in the body.

The device proposed in this invention, including all preferred embodiments achieves best results by operating in contact mode and moving the tissue-contacting surface in a sweeping motion across the tissue and ablating the contacted tissue.

The present invention is further illustrated by the following examples, but is not limited thereby.

Example 1

According to the BPH technique disclosed in the present invention, a procedure was performed on a 30 gr prostate. A twister fiber set, as that described in FIG. 1, was used along with a dual laser source (1470+980 nm) and a commercially available cystoscope. Laser power used was 100 W at the beginning of the treatment, increasing in value to 120 W after 6-7 minutes. The total procedure time was approximately 11 minutes and total energy delivered was 8010.

Example 2

Based on the BPH technique disclosed in the present invention, another procedure was performed on a 45 gr prostate. A twister fiber set, as that described in FIG. 1, was used along a dual laser source (1470 nm+980 nm) and a commercially available cystoscope. Laser power used was 100 W at the beginning of the treatment, increasing value to 130 W after 6-7 minutes. The total procedure time was approximately 15 minutes and total energy delivered was 110 KJ.

In both previous examples, an ablation rate of approximately 2 gr/minute was easily obtained, representing an important improvement over prior art techniques. Considering information from first example, it is estimated that 22 gr out of 30 gr have been removed in the procedure, while in the second it is estimated that 30 gr out of 45 gr have been removed in the procedure.

Procedure can be easily and effectively carried out simply with commercially available cystoscopes for BPH or endoscopes for other applications. A better alternative would be to use a guiding insert at the outlet of the scope tip. It has also been found from experience that the twister fiber is easier to handle than a bare fiber. Gentler, smoother rotations through even 360° are possible and sweeping motions are also more easily accomplished smoothly and effectively, due to both the freely rotating junction at the proximal side of the fiber set as well as the off-axis, bent structure at the distal end.

The asymmetric fiber set of the present invention also can include a means for vibrating the sleeved distal fiber end at a desired, preselected motion and speed to achieve enhanced ablating, excavating action during a treatment.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. An asymmetric, off-axis, radiation-emitting, fiber-optic medical treatment device comprising:
    an optical fiber including a bent tip portion located at a distal end and oriented at an angle with respect to a longitudinal axis of the optical fiber; and
    a sleeve fused to the bent tip portion of the optical fiber.

2. The device according to claim 1, wherein the bent tip portion of the waveguide is shaped so as to focus radiation towards a desired treatment site.

3. The device according to claim 1, comprising two or more optical fibers with bent tip portions which when extended beyond an introducer can rearrange into one or more configurations.

4. The device according to claim 3, comprising 3 to 7 optical fibers with bent tip portions, and wherein a sleeve is fused to each of the bent tip portions of said 3 to 7 optical fibers.

5. The device according to claim 4, wherein said 3 to 7 optical fibers are deployed either in a circular fashion or in a rake fashion.

6. The device according to claim 3, comprising at least 7 optical fibers with small core diameters to aid flexibility and with bent tip portions, wherein said fibers are employed in a close contact arrangement and wherein a sleeve is fused to each of the bent tip portions of the at least 7 optical fibers.

7. The device according to claim 1, further comprising generating means to provide a sweeping motion.

8. The device according to claim 1, further comprising means for vibrating a fiber's distal end in a preselected, planned, essentially automatic motion.

9. The device according to claim 1, wherein at a distal end of the optical fiber, a clad/core and fiber cross-section is expanded compared with these dimensions at a proximal end of the optical fiber.

10. The device according to claim 1,
    wherein the bent tip portion located at the distal end of the optical fiber is oriented at an acute angle relative to the longitudinal axis of the optical fiber, and
    the device further comprising a tissue-contacting surface located at a distal end of the bent tip portion, the tissue-contacting surface being configured to be placed into contact with tissue to be treated,
    wherein the bent tip portion of the optical fiber transmits laser energy from the optical fiber through the tissue-contacting surface to ablate the tissue in contact with the tissue-contacting surface.

11. The device according to claim 10, wherein the tissue-contacting surface is a wear surface that is configured to be placed into contact with the tissue at a treatment site, to transmit laser energy from the optical fiber through the tissue-contacting surface and into the tissue at the treatment site, and wherein the tissue-contacting surface defines a thickness that is sufficient to allow the tissue-contacting surface to wear during ablation of the tissue without preventing the passage of laser energy from the optical fiber therethrough and into the tissue in contact therewith.

12. The device according to claim 11, wherein the acute angle is within the range of about 20° to about 40°.

13. The device according to claim 12, wherein the bent tip portion defines an axial length within the range of about 2 mm to about 5 mm.

14. The device according to claim 11, wherein the sleeve extends annularly about the bent tip portion and forms at least a portion of the tissue-contacting surface.

15. The device according to claim 14, wherein optical fiber defines an emitting face, and the sleeve extends annularly about and is substantially flush with the emitting face, and the emitting face of the optical fiber and the sleeve define the tissue-contacting surface.

16. The device according to claim 15, wherein the optical fiber includes an axially-extending core defining the emitting face, and the emitting face of the core and a distal portion of the sleeve define the tissue-contacting surface.

17. The device according to claim 16, wherein the distal portion of the sleeve defining the tissue-contacting surface is curvilinear.

18. The device according to claim 17, wherein the emitting face defining the tissue-contacting surface is curvilinear and is substantially flush with the distal portion of the sleeve.

19. The device according to claim 16, wherein the sleeve extends annularly and axially throughout the bent tip portion of the optical fiber and a portion of the optical fiber proximal to the tip portion.

20. The device according to claim 19, wherein the optical fiber includes a core and a cladding, and the sleeve and outer portion of the cladding are made of substantially the same material.

21. The device according to claim 20, wherein the outer portion of the cladding is made of glass, the sleeve is made of glass, and the sleeve is thermally fused to the cladding substantially throughout the interface between the sleeve and the cladding.

22. The device according to claim 14, wherein the sleeve forms a cap that encloses the distal end of the optical fiber, the distal end of the cap forms the tissue-contacting surface, the distal end of the optical fiber defines an emitting face that transmits laser energy therethrough and the tissue-contacting surface of the cap for transmitting the laser energy into tissue in contact with the tissue-contacting surface.

23. The device according to claim 22, wherein the tissue-contacting surface of the cap defines a thickness that is sufficient to wear during ablation of tissue in contact therewith without forming a hole therethrough.

24. The device according to claim 23, wherein the tissue contacting surface of the cap defines a thickness within the range of about 1 mm to about 4 mm.

25. The device according to claim 24, wherein the optical fiber includes a core and a cladding, and the cap and outer portion of the cladding are made of substantially the same material.

26. The device according to claim 25, wherein the outer portion of the cladding is made of glass, the sleeve is made of glass, and the sleeve is thermally fused to the cladding substantially throughout the interface between the sleeve and the cladding.

* * * * *